US00PP22181P2

(12) United States Plant Patent
Petit

(10) Patent No.: US PP22,181 P2
(45) Date of Patent: Oct. 4, 2011

(54) ***HEMEROCALLIS* PLANT NAMED 'SPD 06-02'**

(50) Latin Name: ***Hemerocallis* hybrid**
Varietal Denomination: SPd 06-02

(76) Inventor: Ted L. Petit, McIntosh, FL (US)

( * ) Notice: Subject to any disclaimer, the term of this patent is extended or adjusted under 35 U.S.C. 154(b) by 0 days.

(21) Appl. No.: 12/802,614

(22) Filed: Jun. 10, 2010

(51) Int. Cl.
*A01H 5/00* (2006.01)

(52) U.S. Cl. ..... Plt./312

(58) Field of Classification Search ..... Plt./312
See application file for complete search history.

*Primary Examiner* — Susan McCormick Ewoldt
(74) *Attorney, Agent, or Firm* — Penny J. Aguirre

(57) ABSTRACT

A new cultivar of *Hemerocallis* named 'SPd 06-02', characterized by its flowers that are 10 cm in diameter, golden yellow in color with maroon to burgundy red eyezones and green throats, its flowers that fully open under cool growing conditions and are self cleaning, its flower petals that are triangular in shape, heavy in substance, and have lightly ruffed edges, its blooming habit that commences very early in the season with continuous rebloom until frost on recurrent, branched scapes with high bud counts, its foliage that is evergreen, semi-evergreen or dormant depending on the growing climate with suitability in a variety of growing climates, its compact plant habit with grass-like foliage, its fast multiplication rate, and its hardiness in U.S.D.A. Zones 3 to 11, and its resistance to daylily rust.

2 Drawing Sheets

Botanical classification: *Hemerocallis* hybrid.
Cultivar designation: 'SPd 06-02'.

BACKGROUND OF THE INVENTION

The present invention relates to a new and distinct cultivar of *Hemerocallis* plant of hybrid origin, botanically known as *Hemerocallis* 'SPd 06-02' and will be referred to hereafter by its cultivar name, 'SPd 06-02'.

The new cultivar was developed through on on-going breeding program conducted by the Inventor in McIntosh, Fla. The objectives of the breeding program are to develop new cultivars of tetraploid *Hemerocallis* that exhibit early and continuous flowering on recurrent, branched scapes with high bud counts and flowers that fully open during cool conditions, have bright flower color, heavy petal substance, and clean shedding of the old flowers to allow new buds to fully develop. Further objectives of the breeding program include developing plants that exhibit a high multiplication rate, short blooms stalks, foliage that is grass-like and compact, cold and heat hardiness and resistance to daylily rust.

The Inventor made crosses in summer of 2005 between specific unnamed proprietary male and female parents in his breeding line and pooled all the resulting seed from his crosses and evaluated the resulting seedlings based on the objectives of the breeding program. 'SPd 06-02' was selected as a single unique plant from the resulting seedlings in summer of 2006. The specific parents are unknown.

Asexual reproduction of the new cultivar was first accomplished by division in McIntosh, Fla. in 2006 by the Inventor. Propagation by division and tissue culture has determined that the characteristics of this cultivar are stable and are reproduced true to type in successive generations.

SUMMARY OF THE INVENTION

The following traits have been repeatedly observed and represent the characteristics of 'SPd 06-02'. These attributes in combination distinguish 'SPd 06-02' as a new and distinct cultivar of *Hemerocallis*.

1. 'SPd 06-02' exhibits flowers that are about 10 cm in diameter (4 inches) and are golden yellow in color with maroon to burgundy red eyezones with green throats.
2. 'SPd 06-02' exhibits flower petals that are triangular in shape, heavy in substance, and have lightly ruffed edges.
3. 'SPd 06-02' exhibits a blooming habit that commences very early in the season with continuous rebloom until frost on recurrent, branched scapes with high bud counts.
4. 'SPd 06-02' exhibits flowers that fully open under cool growing conditions and cleanly shed spent flowers to allow new buds to fully develop.
5. 'SPd 06-02' has foliage that is evergreen, semi-evergreen or dormant depending on the growing climate, which allows its suitability to a variety of growing climates.
6. 'SPd 06-02' is a tetraploid.
7. 'SPd 06-02' exhibits a compact plant habit with grass-like foliage.
8. 'SPd 06-02' is readily propagated by division or tissue culture and exhibits a fast multiplication rate.
9. 'SPd 06-02' is cold and heat hardy in U.S.D.A. Zones 3 to 11.
10. 'SPd 06-02' is resistant to daylily rust (*Puccinia hemerocallidis*).

The new cultivar can be most closely compared to the cultivars 'Black Eyed Stella' (not patented) and 'Little Cadet' (not patented). Both cultivars are similar to 'SPd 06-02' in flower coloration and in shedding spent blooms. Both cultivars differ from 'SPd 06-02' in having foliage that goes dormant under all conditions, in having taller and un-branched flower scapes, in having less abundant flowers that are smaller in size and do not open fully in cold weather, in blooming later in the season with less recurrent blooming, in having wider and taller foliage that lacks daylily rust resistance,. and in having a slower multiplication rate.

BRIEF DESCRIPTION OF THE DRAWING

The accompanying colored photograph illustrates the overall appearance and distinct characteristics of the new

*Hemerocallis*. The photograph was taken of a two year-old plant of 'SPd 06-02' as grown outdoors in a field plot from a single fan in McIntosh, Fla. and was grown without fungicide treatment or deadheading.

Figure 1:
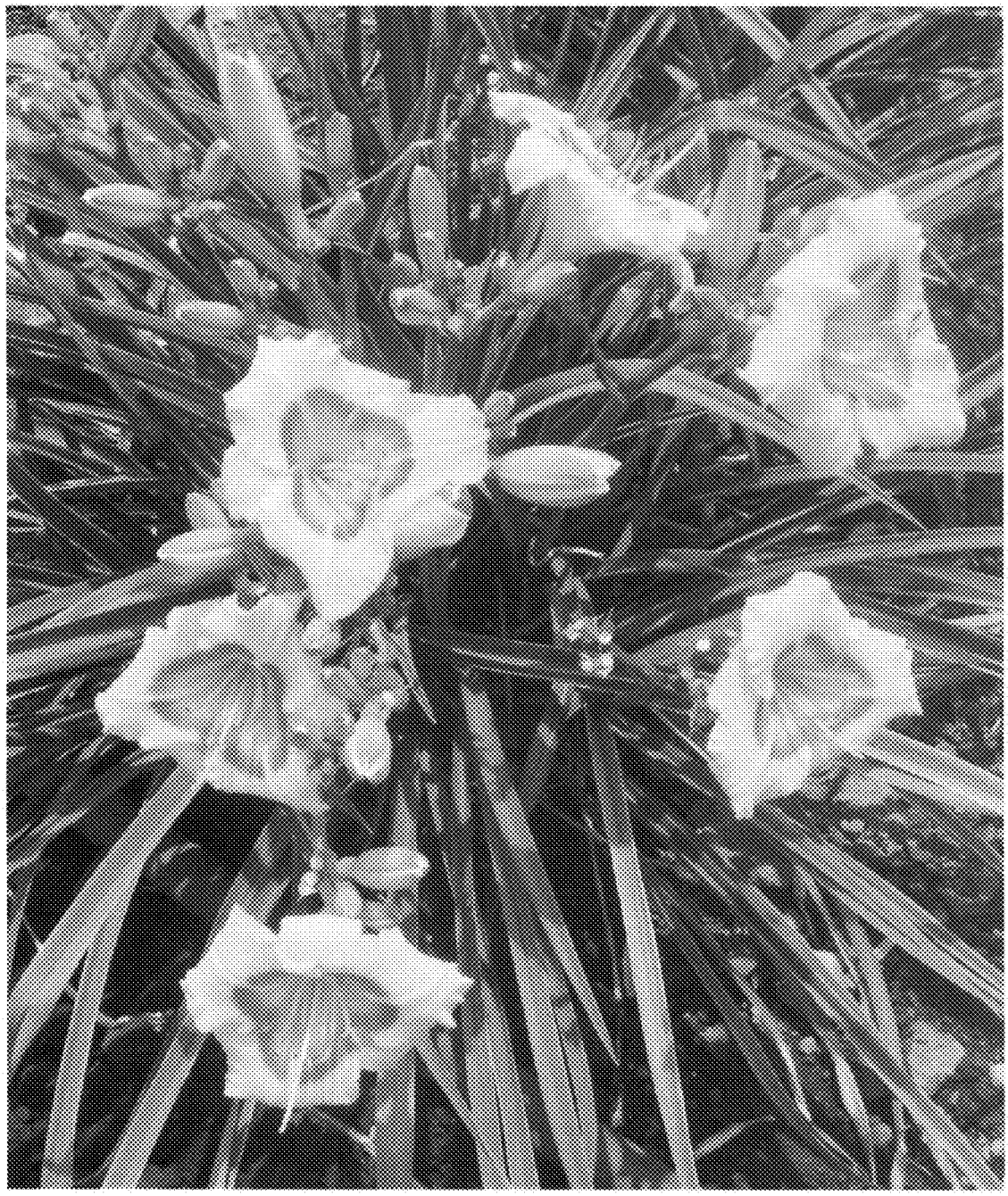

The photograph in FIG. 1 was taken in May and illustrates the early flowering, prolific flowering, high bud counts, short-branched scapes, self-cleaning of blooms, and fast growth rate of 'SPd 06-02'.

Figure 2:
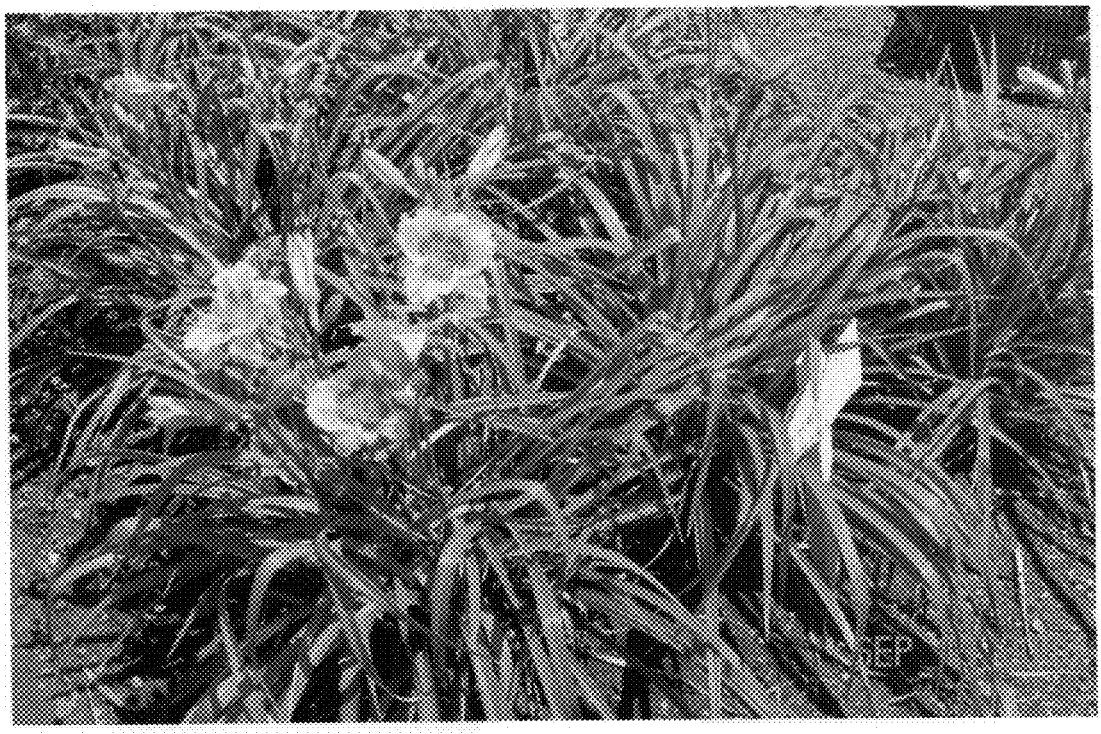

The photograph in FIG. 2 was taken in September and is provided to show its continued strong blooming habit of 'SPd 06-02' through the end of the growing season.

Figure 3:
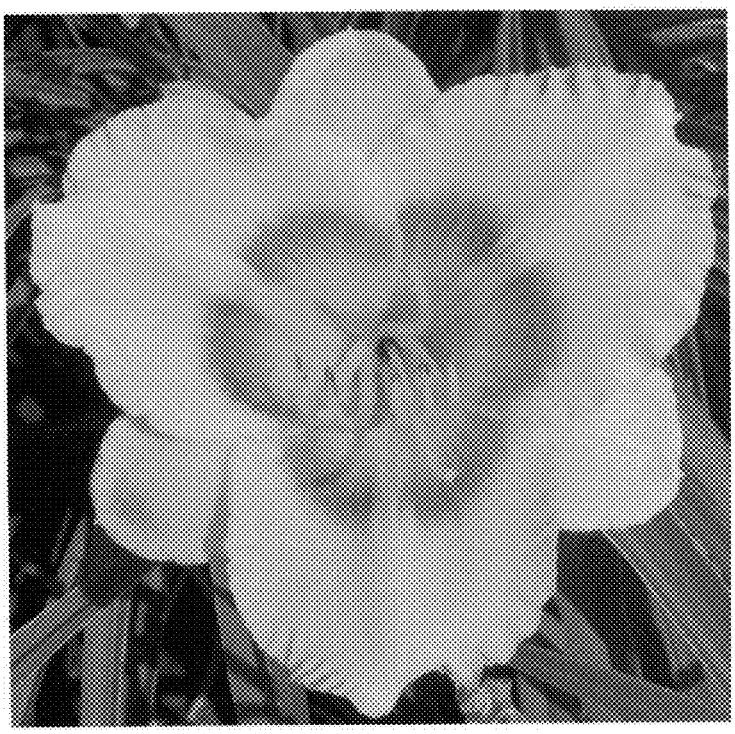

The photograph in FIG. 3 provides a close-up view of a flower of 'SPd 06-02'. The colors in the photographs are as close as possible with the digital photography and printing techniques utilized and the color codes in the detailed botanical description more accurately describe the new *Hemerocallis*.

DETAILED BOTANICAL DESCRIPTION OF THE PLANT

The following is a detailed description of a 2 year-old plant of the new cultivar as grown outdoors in a 1-gallon container in McIntosh, Fla. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General characteristics:

- *Blooming period.*—Commencing in March and recurrent until frost in Florida.
- *Plant habit.*—Herbaceous perennial, compact grass-like foliage.
- *Height and spread.*—Reaches 30 to 40 cm in height and spread, flower scapes about the same height as foliage height.
- *Hardiness.*—U.S.D.A. Zones 3 to 11.
- *Diseases and pests.*—Has been observed to be resistant to daylily rust (*Puccinia hemerocallidis*).
- *Root description.*—Fibrous roots.
- *Propagation.*—Division and tissue culture.
- *Growth rate.*—Vigorous with a high multiplication rate (5 fans per fan per season).

Foliage description:

- *Leaf shape.*—Linear.
- *Leaf division.*—Simple.
- *Leaf base.*–Sheathed to crown.
- *Leaf apex.*—Narrowly acute.
- *Leaf venation.*—Longitudinal, parallel, not prominent, same color as leaves.
- *Leaf margins.*—Entire.
- *Leaf attachment.*—Sheathed, not petiolate.
- *Leaf arrangement.*—Equitant, fan-shaped.
- *Leaf orientation.*—Held upright and slightly pendulant from mid section towards apex once matured.
- *Leaf surface.*—Glabrous to slightly glaucous.
- *Leaf color.*—Young leaves (upper and lower surface); a blend of 137C and 144A, mature leaves (upper and lower surface); a blend of 137B and 144A.
- *Leaf size.*—Up to 42 cm in length, 0.5 to 3.5 cm in width.
- *Leaf quantity.*—About 65 leaves per 1-gallon container.

Flower scape description:

- *Scape shape.*—Round, slightly ovoid, pithy.
- *Scape number.*—1 to 2 per fan at one time, continuously produced until frost.
- *Scape aspect.*—Straight, held upright.
- *Scape size.*—An average of 26 cm in length and 5 cm in width, with branches an average of 3 cm in length and 4 mm in width.
- *Scape color.*—137A.
- *Scape surface.*—Glabrous, slightly glaucous.
- *Scape branching.*—1 to 2 branches per scape, internode length about 2 cm.
- *Scape leaves.*—1 per branch point, 146B in color, 2 cm to 4.7 cm in length, 1 cm to 1.8 cm in width, sheathed base, acuminate apex, glabrous to slightly glaucous surface.

Flower description:

- *Inflorescence type.*—Scape bearing an average of 4 single flowers per scape, one flower is open at a time.
- *Inflorescence size.*—Varies with opening of flowers, an average of 12 cm in width and 5 cm in depth.
- *Lastingness of flowers.*—About 24 hours, self cleaning.
- *Flower size.*—An average of 5 cm in depth and 10 cm in diameter.
- *Flower fragrance.*—None.
- *Flower number.*—1 to 4 per inflorescence.
- *Flower aspect.*—Upright to outward.
- *Flower bud color.*—21C with fine lines of 144A and 144B at base and apex, 147B at very apex.
- *Flower bud shape.*—Oblong.
- *Flower attachment.*—Petiolate.
- *Petal number.*—3.
- *Petal shape.*—Broadly lanceolate (triangular).
- *Petal color.*—Upper and lower surface 17A with eye-zone (6 mm in width) N34 and throat N144C.
- *Petal surface.*—Glabrous, waxy, mid-vein deeply grooved in upper surface.
- *Petal margins.*—Entire, strongly crenate, lightly ruffled.
- *Petal apex.*—Obtuse.
- *Petal size.*—Average of 5 cm in length and 3.3 mm in width.
- *Petal aspect.*—Slightly recurved.
- *Sepal number.*—3.
- *Sepal shape.*—Elliptic to broadly lanceolate, moderately recurved.
- *Sepal margin.*—Entire, very slightly ruffled.
- *Sepal size.*—Average of 6.2 cm in length, 2 cm in width.
- *Sepal aspect.*—Moderately recurved.
- *Sepal surface.*—Glaucous.
- *Sepal apex.*—Acute.
- *Sepal base.*—Fused.
- *Sepal color.*—Upper surface 16A, N144A towards base with a transverse mid-section 3 mm in width N34; lower surface 16A, N144 towards base.
- *Pedicel size.*—Average of 2.5 cm in length and 4 mm in width.
- *Pedicel shape.*—Round.
- *Pedicel strength/aspect.*—Moderately strong, held at about 20° relative to peduncle.
- *Pedicel color.*—137A.

Reproductive organs:

- *Gynoecium.*—1 pistil, about 5.7 cm in length and 1.5 mm in width, base 11B in color, apex 14C in color, stigmas; capitate, 15A in color, ovary; 0.6 cm in length and 4 mm in width, 138B in color.

*Androcoecium.*—Stamens; 6, anthers; 7 mm in length and 2 mm in width, N167A in color; filament; 3.8 cm in length, 2 mm in width at base and tapered to 1 mm at tip, base and apex 18B in color, mid-section 166C in color, pollen; moderate in quantity and 17A in color.

*Fruit/seeds.*—None observed.

It is claimed:

1. A new and distinct cultivar of *Hemerocallis* plant named 'SPd 06-02' as herein illustrated and described.

* * * * *